United States Patent [19]

Arduengo

[11] Patent Number: 5,034,464
[45] Date of Patent: Jul. 23, 1991

[54] AMINE-BORANE ADDUCT CURING AGENTS FOR EPOXY/ANHYDRIDE RESINS

[75] Inventor: Anthony J. Arduengo, Wilmington, Del.

[73] Assignee: E. I. Du Pont de Nemours and Company, Wilmington, Del.

[21] Appl. No.: 387,362

[22] Filed: Jul. 19, 1989

[51] Int. Cl.$^5$ .................. C08L 25/08; C08L 33/02
[52] U.S. Cl. .................. 525/207; 525/117; 525/119; 525/194
[58] Field of Search .............. 525/207, 117, 119, 194

[56] References Cited

U.S. PATENT DOCUMENTS

| | | | |
|---|---|---|---|
| 3,255,153 | 6/1966 | McCloskey | 260/47 |
| 3,347,827 | 10/1967 | Lee, Jr. | 528/97 |
| 4,092,373 | 5/1978 | Siwiec et al. | 525/207 |
| 4,251,422 | 2/1981 | Hertler | 260/31.2 N |
| 4,816,500 | 3/1989 | Corcoran | 525/117 |

FOREIGN PATENT DOCUMENTS 242064  1/1988  Czechoslovakia .

OTHER PUBLICATIONS

Plesek et al., "Method for Tertiary Aminoborane Production," *Chemical Abstracts*, vol. 108, Abstract No. 153086f.

*Primary Examiner*—John C. Bleutge
*Assistant Examiner*—Robert E. L. Sellers, II

[57] ABSTRACT

An improved curing agent for use in coatings, laminates, moldings, castings and adhesives comprising the use of an amine-borane adduct along with a mixture of an anhydride polymer or copolymer having at least two anhydride groups and an epoxy polymer or copolymer having at least two epoxy groups. Also provided is an improved process for the preparation of tertiary amine borane curing agents.

16 Claims, No Drawings

AMINE-BORANE ADDUCT CURING AGENTS FOR EPOXY/ANHYDRIDE RESINS

BACKGROUND OF THE INVENTION

1. Field of the Invention

This invention relates to curing agents for epoxy/anhydride resins. There are a wide variety of two component compositions available for finishing substrates. Generally, the mixing of the components occurs before application, and addition of a curing agent results in a product with a relatively short (several hour) shelf life. The present invention which teaches the use of amine-borane adducts as curing agents improves the usable time in which the composition can be applied to a substrate at the application stage and offers short cure times and harder surfaces.

Also provided is an improved process for the preparation of tertiary amine borane adduct curing agents.

Resins containing the curing agents of the current invention are used in coatings, laminates, moldings, castings and adhesives.

2. Prior Art

Commonly assigned patent application Ser. No. 07/051,867 U.S. Pat. No. 4,816,500 discloses and claims a coating composition containing 20–80% by weight of reactive binder components and 80–20% by weight of an organic carrier; the binder contains about (a) 50–95% by weight, based on the weight of the binder, of an acrylic polymer having at least two reactive anhydride groups which consist of polymerized monomers of an ethylenically unsaturated anhydride and polymerized monomers selected from the group consisting or alkyl methacrylate, alkyl acrylate and any mixtures thereof, wherein the alkyl groups have 1–8 carbon atoms and the polymer has a weight average molecular weight of about 2,000–50,000; (b) 5–50% by weight, based on the weight of the binder, of a glycidyl component having at least two reactive glycidyl groups; and the composition contains about 0.1–5% by weight, based on the weight of the binder, of a catalyst (curing agent); and wherein the primary reaction on curing of the composition occurs between the anhydride groups of the acrylic polymer and the glycidyl groups of the glycidyl component and wherein the composition upon curing forms a hard glossy and tack free finish.

The useable time in which the composition can be applied by conventional means such as that in Ser. No. 07/051,867 is about 1 to 6 hours depending on the surrounding temperature conditions.

U.S. Pat. No. 3,013,016 describes the synthesis of trialkylamine borane adducts using sodium or potassium borohydride, an acid such as carbon dioxide, the parent amine and a water immiscible solvent. Water is also present during the reaction.

Czech Patent 242,064 also describes a process for the preparation of tertiary amine borane adducts in which a metal borohydride, carbon dioxide, a tertiary amine and a solvent are mixed (the borohydride is present as a suspension), allowed to react, and then the reaction mixture is washed with water, and the solvent evaporated. Absence of water during the reaction step eliminates the potential side reaction of the borohydride with water.

SUMMARY OF THE INVENTION

The present invention describes the use of amine-borane adducts as curing agents for epoxy/anhydride resins. These can be used either alone or in combination with a borane-free amine curing agent. These improved curing agents offer (i) improvement in the useable time in which the composition can be applied by conventional means such as spraying.

(ii) fast cure with improved hardness of the finish.

The amine borane adduct curing agents are made by an improved process, wherein a tertiary amine is reacted with an alkali metal borohydride and carbon dioxide in an organic solvent, wherein the improvement is that the reaction and subsequent isolation of the product are done in the substantial absence of water.

DETAILS OF THE INVENTION

The present invention describes the use of amine-borane adducts as curing agents for epoxy/anhydride resins which are used in paints, coatings, laminates, moldings, castings and adhesives. These curing agents improve the useable time in which the composition can be applied to a substrate by conventional means such as spraying and after application allow for fast cure and improved hardness of the finish. During curing a primary reaction between the anhydride groups of the anhydride polymer of copolymer and the epoxy groups of the epoxy polymer or copolymer occurs.

Typically, the reactive components used for making an epoxy/anhydride resin are an anhydride bearing polymer or copolymer and an epoxy bearing polymer or copolymer. The anhydride or epoxy bearing polymers may be in a solvent. These components, along with a catalyst (curing agent) are often provided to the user in separate containers and are mixed on demand.

The anhydride component, of the epoxy/anhydride resins which are useful for the curing agents of this invention, may be any polymer or copolymer with a weight average molecular weight of $\leq 100,000$ containing at least two reactive anhydride groups Preferred anhydride components are copolymers prepared from one or more of the monomers of styrene, methacrylates, or acrylates with one or more of the monomers of itaconic acid, itaconic anhydride, maleic anhydride or isobutenyl succinic anhydride. After formation of the polymer the itaconic acid which is contained in the polymer is converted to the anhydride.

The epoxy component, of the epoxy/anhydride resins which are useful for the curing agents of this invention, may be any polymer or copolymer with a weight average molecular weight of $\leq 100,000$ containing at least two epoxy groups.

Preferred epoxy components are copolymers prepared from methacrylates with glycidylmethacrylate in combination with the polyglycidylethers of sorbitol.

The coating composition formed using the components described may contain 20% to 80% of the polymer or copolymer having at least two anhydride groups and 80% to 20% of the polymer or copolymer having at least two epoxy groups.

Neither component should contain any substituents which would interfere with the curing process.

Any amine-borane adduct can be used in the instant invention. Preferred amine-borane adducts are those containing tertiary amines and include 1,4-diazabicyclo[2.2.2]octane-monoborane, 2-methyl-1,4-diazabicyclo[2.2.2]octane-monoborane, alkyl substituted 1,4-diazabicyclo[2.2.2]octane-monoborane wherein the alkyl groups contain up to about 6 carbon atoms, N,N,N',N'-tetramethylethylenediamine-monoborane, N,N-dimethyl-1,3-propanediamine-monoborane, N,N-dimethyl ethanol amine-borane, N,N-diethyl ethanol amine-borane, N,N-dibutyl ethanol amine-borane, N,N-diethyl hexanol amine-borane.

Especially preferred adducts are 1,4-diazabicyclo[2.2.2]octane-monoborane and alkyl substituted 1,4-diazabicyclo[2.2.2]octane-monoborane wherein the alkyl groups contain up to about 6 carbon atoms. The most preferred adducts are 1,4-diazabicyclo[2.2 2]-octane-monoborane and 2-methyl-1,4-diazabicyclo[2.2.2]octane-monoborane and/or mixtures thereof.

The amine-borane adducts of this invention can be made by direct interaction of the amines with borane-dimethylsulfide complex or borane-THF complex or by the procedures disclosed by VanPaasschen et al., Canadian Journal of Chemistry, 53, 723–726 (1975); Gatti et al., Inorganic Chemistry, 5, 2075–2076 (1966) or Brown, et al., Inorganic Chemistry, 19, 455–457 (1980) or, preferably, by the method described below (p. 6).

In using amines which contain more than one nitrogen in the molecule, it is to be understood that one, several, or all of the nitrogens may be complexed with borane.

The concentration of amine-borane adducts contained in the epoxy/anhydride composition can range from 1 to 6% by weight.

The amine-borane adducts can be used as the sole catalyst or blended with borane-free amines.

Use of the amine-borane adducts in place of the parent amines as curing agents for epoxy/anhydride resins increases the useable time in which the composition can be applied by conventional means and, after application, still offers short cure times and improved hardness of the finish.

Tertiary amine borane adducts are made by an improved process, by reacting an alkali metal borohydride, carbon dioxide, and a tertiary amine in an organic solvent, the improvement being the substantial absence of water during the reaction and the isolation of the amine borane adduct. The improved process gives very high yields of the tertiary amine borane adduct, and the product is often purer than from prior art processes. In addition, fewer steps are required in the improved process, giving it an economic advantage over prior art processes.

Preferred alkali metal borohydrides are lithium borohydride, sodium borohydride and potassium borohydride. Any organic solvent that dissolves the amine and amine borane adduct is satisfactory, provided it does not react with any of the reactants or products. It is preferred that the solvent does not dissolve the inorganic by-product. A low boiling point solvent is desirable so it can be easily removed during the isolation step. Suitable solvents include hydrocarbons such as toluene, halogenated hydrocarbons such as carbon tetrachloride and nitriles such as acetonitrile and benzonitrile. Nitriles are preferred solvents, and acetonitrile is especially preferred. Solvents that form very stable adducts with borane are not suitable.

By substantial absence of water is meant that the starting materials are dry, that is contain less than about 1.0% water and preferably less than 0.1% water and most preferably less than 0.05% water, and that the reaction and isolation are done under conditions under which substantial amounts of water cannot enter the reaction (as from the atmosphere) such that the above low water levels are maintained throughout the reaction and isolation of the amine borane adduct. It is therefore preferred to carry out the process under an inert gas such as nitrogen or argon to the greatest extent practicable. Short exposures to the atmosphere are not harmful.

To carry out the process, the tertiary amine, alkali metal borohydride and solvent are added to the reaction vessel and stirred. The proportions of alkali metal borohydride to tertiary amine are usually about 1:1 on a molar basis (substantially different ratios can be used, but result in a waste of materials) if a monoborane adduct is desired. Monoborane adducts are preferred, but bisborane adducts of diamines can also be made. The proportion of solvent used is not critical, but enough should be used so that a smooth easily stirred slurry is formed (the inorganic borohydrides and by-product salts are substantially insoluble in the organic solvent). The mixture is then stirred (vigorous stirring is desirable) while carbon dioxide is added as by bubbling into the liquid or passing over the surface of the liquid for, typically, 1 to 5 hours until the reaction is complete (uptake of carbon dioxide ceases). The temperature during this time is about $-10°$ C. to the boiling point of the solvent or tertiary amine, whichever boiling point is lower, providing of course that the reactants and products are stable at the boiling point of the solvent or tertiary amine A preferred range is ambient temperature to about 50° C. The product is then isolated by filtering off the inorganic by-product, and removing the solvent as by distillation or evaporation. Further illustration of the process will be found in the Examples.

Although any tertiary amine borane adduct may be made by the above method (assuming the monoborane adduct of the amine is stable), it is especially useful for preparing the monoborane adducts of 1,4-diazabicyclo[2.2.2]octane and alkyl substituted 1,4-diazabicyclo[2.2.2]octanes wherein the alkyl groups contain up to about 6 carbon atoms. It is most useful for preparing the monoborane adducts of 1,4-diazabicyclo[2.2.2]octane and 2-methyl-1,4-diazabicyclo[2.2.2]octane.

EXPERIMENT 1

Preparation of 1,4-Bicyclo[2.2.2]octane-Monoborane Use of $(CH_3)_2S:BH_3$ Complex In the hood, a 0.5 l 3-neck round bottom flask was charged with 19.1 g (0.17 mol) 1,4-diazabicyclo[2.2.2]octane and a stirbar. The 1,4-diazabicyclo[2.2.2]octane was dissolved in approximately 250 ml of toluene. A nitrogen purge was started through the solution via a gas dispersion tube. The nitrogen was exited through a dry ice trap. To the 1,4-diazabicyclo[2.2.2]octane solution was added, via syringe, 10.0 ml of refrigerated 10M borane-dimethyl sulfide complex. A crystalline solid began forming just after the addition was complete. While stirring, the solution was heated to drive off any remaining dimethyl sulfide. The solution was cooled to room temperature, allowing more solid to recrystallize, then filtered through a fritted glass funnel under a nitrogen blanket. A $^1$H NMR spectrum of the first crop (8.00 g, mp 164°–165° C.) showed it to be 1,4-diazabicyclo[2.2.2]octane-monoborane. A second crop of product (4.48 g, mp 164°165° C/) was collected. Total yield was 12.48 g (99%).

EXPERIMENT 2

Preparation of 1,4-Diazabicyclo[2.2.2]octane-Monoborane Use of $C_4H_8O:BH_3$ Complex In the hood, a 2 l round bottom flask was charged with 89.6 g (0.8 mol) 1,4-diazabicyclo[2.2.2]octane and a stirbar. A minimal amount of dry THF [C₄H₈O] was added to stir the 1,4-diazabicyclo[2.2.2]octane and the flask was capped with a supa seal septa. The slurry was kept cool via an ice bath. To the cold slurry was added, via cannula over approximately 45 minutes, 800 ml of 1M borane-THF complex. The mixture was warmed to room temperature and stirred for 3 hours. The solution was then taken into the drybox and filtered through a fritted funnel. [A 150 ml or larger funnel was required to contain the filtered solids]. Additional solvent was removed from the filtrate by evaporation and a second crop of crystals was collected by filtration. First crop yield was 34.03 g, mp 159°–162° C., second crop yield was 33.95 g, mp 160°–163° C. $^1$H NMR's of both solids shows them to be the desired 1,4-diazabicyclo[2.2.2]octane-monoborane.

EXAMPLE 1

Resin Preparation #1 [Anhydride Component]

The following ingredients were charged to a reactor equipped with a thermometer, stirrer, dropping funnel, water separator, nitrogen purge and condenser.

| Portion 1 | |
|---|---|
| Xylene | 232.10 g |
| Portion 2 | |
| Styrene | 91.70 g |
| Butylmethacrylate | 122.20 g |
| Butylacrylate | 232.2 g |
| Xylene | 50.20 g |
| Portion 3 | |
| Itaconic acid | 191.60 g |
| Xylene | 60.00 g |
| Portion 4 | |
| 75% Tert-butylperoxyacetate | 30.50 g |
| Propyleneglycolmonomethyletheracetate | 12.10 g |
| Xylene | 57.50 g |
| Portion 5 | |
| Propyleneglycolmonomethyletheracetate | 102.10 g |
| Portion 6 | |
| Propyleneglycolmonomethyletheracetate | 102.10 g |

Portion 1 was added to the reactor and heated to reflux. Portion 2 was premixed and fed to the reactor over three hours simultaneous with portion 3. Portion 3 was predispersed to form a pumpable slurry and fed to the reactor over three hours simultaneous with portion 2. Portion 4 was premixed and fed to the reactor over 3 hours and 20 minutes starting with the start of portion 2. The batch was maintained at reflux until 25.2 g of water was collected in the water separator. Portion 5 was then added to the batch and 341.3 g of solvent removed by distillation. Portion 6 was then added to the reaction mixture.

Resin Preparation #2 [Epoxy Component]

The following ingredients were charged to a reactor equipped with a thermometer, stirrer, dropping funnel, nitrogen purge and condenser.

| Portion 1 | |
|---|---|
| Butylacetate | 148.93 g |
| Toluene | 25.51 g |
| Ethylacetate | 41.39 g |
| Portion 2 | |
| Glycidylmethacrylate | 233.12 g |
| Butylacetate | 6.25 g |
| Butylmethacrylate | 155.41 g |
| Portion 3 | |
| Vazo 67 initiator from Du Pont | 18.68 g |
| Butylacetate | 56.03 g |
| Portion 4 | |
| Vazo 67 initiator from Du Pont | 4.77 g |
| Butylacetate | 14.32 g |
| Portion 5 | |
| Butylacetate | 95.75 g |
| Propyleneglycolmonomethyletheracetate | 48.32 g |

Portion 1 was added to the reactor and heated to reflux. Portion 2 was premixed and added to the reactor over 2 hours simultaneous with portion 3. Portion 3 was premixed and added to the reactor over two hours simultaneous with portion 2. Portion 4 was added to the reactor over 30 minutes after the completion of portion 2 and 3. The reaction was held at reflux for 30 minutes. Portion 5 was added to the mixture and blended in.

Coating Compositions

The following compositions were made by thoroughly blending the following ingredients:

| Ingredients | A | B | C |
|---|---|---|---|
| Resin #1 | 23.2 g | 22.95 g | 23.26 g |
| Resin #2 | 12.86 g | 12.72 g | 12.89 g |
| Araldite GY-358 (Sorbitol Polyglycidylether from Ciba-Geigy) | 2.44 g | 2.41 g | 2.45 g |
| 1,4-Diazabicyclo[2.2.2]-octane | 0 g | 0 g | 0.49 g |
| 1,4-Diazabicyclo[2.2.2]-octane-monoborane | 0.54 g | 0.81 g | 0 g |
| Butylacetate | 10.93 g | 11.09 g | 10.90 g |

These coating compositions were applied to a glass substrate by draw downs with a 0.010 inch blade and allowed to cure at room temperature. Gel times were run in a Gardner-Holdt tube. Hardness was determined with a persoz hardness pendulum.

The results are given below:

| Modification | A | B | C |
|---|---|---|---|
| Gel Time | 23 hours | 15 hours | 5 hours |
| Persoz Hardness (7 Day) | 110 | 121 | 100 |
| Film Thickness (microns) | 72 | 69 | 70 |

The results clearly show that the useable time in which the composition can be applied by conventional means as measured by the gel time for the coating mixture containing 1,4-diazabicyclo[2.2.2]octane-monoborane as the curing agent is 3 to 4.6 times that of the coating mixture containing 1,4-diazabicyclo[2.2.2]octane as the curing agent. Also the coating mixture containing the 1,4-diazabicyclo[2.2.2]octane-monoborane as the curing agent has resulted in the formation of a finish with a harder surface.

EXAMPLE 2

Preparation of Hydroxyl Functional Polymer A

The following ingredients were charged to a reactor equipped with a thermometer, stirrer, dropping funnel, water separator, nitrogen purge and condenser.

| Portion 1 | |
|---|---|
| Methyl amyl ketone (MAK) | 384.064 g |
| Portion 2 | |
| Methyl methacrylate | 94.970 g |
| Hydroxy ethyl acrylate | 189.940 g |
| Styrene | 94.970 g |
| Butyl acrylate | 253.230 g |
| Portion 3 | |
| Methyl amyl ketone | 45.200 g |
| Butyl peracetate | 21.080 g |

Portion 1 was charged to the reactor, covered with nitrogen and heated to reflux temperature. Portions 2 and 3 were then fed simultaneously upon reaching reflux. Portion 2 is fed at a rate of 2.82 g/min. over a 225 min. period, and portion 3 is fed at 0.264 g/min. over 240 mins. The reaction is then held at reflux for 30 mins. at the conclusion of portion 3. At the end of the 30 min., 218.454 g of MAK are recovered to bring the resulting polymer to 75% solids and a Gardner-Holdt viscosity of Z-Z2.

| Preparation of Glycidyl Functional Acrylic Polymer B | |
|---|---|
| Portion 1 | |
| Glycidyl methacrylate | 8.560 g |
| Butyl acrylate | 16.370 g |
| Methyl methacrylate | 10.740 g |
| Xylene | 120.536 g |
| Portion 2 | |
| Glycidyl methacrylate | 169.950 g |
| Butyl acrylate | 136.610 g |
| Methyl methacrylate | 167.770 g |
| Xylene | 14.484 g |
| Portion 3 | |
| Xylene | 83.450 g |
| Butyl peracetate | 22.530 g |

Portion 1 was charged to the reactor, covered with nitrogen and heated to reflux temperature. Portion 2 and 3 were individually premixed and charged simultaneously over a 300 min. period. Upon completion of the feed, the reaction mixture is held at reflux for 45 mins.

The resulting polymer had a weight solids content of 69.0–71.0% at a Z-Z2 Gardner-Holdt viscosity. The polymer had a weight average molecular weight of 5,000–7,000.

| Preparation of White Dispersion | |
|---|---|
| Portion 1 | |
| Hydroxyl functional polymer A | 5.500 g |
| Methyl amyl ketone | 14.260 g |
| Portion 2 | |
| TiO$_2$ White pigment | 70.000 g |
| Portion 3 | |
| Hydroxyl functional polymer A | 7.840 g |
| Methyl amyl ketone | 2.400 g |

Portion 1 was added to the blend tank while mixing at low speed and then mixed for 10 minutes. Portion 2 was added to the blend tank while mixing at low speed and then mixed for 20 minutes at high speed. Portion 3 was added to the tank at low speed and then mixed at high speed after the last addition. The resulting blend was then put through a sand mill for fineness.

Preparation of Coating Composition

A coating composition was prepared by thoroughly blending together the following components:

| Portion 1 | |
|---|---|
| White Dispersion | 301.17 g |
| Denecol EX-622 (Nagase) Epoxy Ether | 43.68 g |
| Araldite CY-184 (Ciba-Geigy) Epoxy Ether | 48.56 g |
| Glycidyl Functional Acrylic Polymer B | 32.03 g |
| Silicone SF-69 (General Electric) | 0.18 g |
| Portion 2 | |
| Resin Preparation #1 (Anhydride Component) [From Example 1] | 353.60 g |

| Preparation of Curing Agent Solutions | | | | |
|---|---|---|---|---|
| | Standard | Control | A | B |
| Ethanol | 73.81 g | 73.81 g | 55.86 g | 46.25 g |
| n-Butanol | 7.64 g | 7.54 g | — | — |
| Butyl Carbitol | 46.93 g | 46.93 g | 46.95 g | 30.99 g |
| 1,4-Diazabi-cyclo[2.2.2]-octane | 11.92 g | 5.96 g | 5.96 g | 5.96 g |
| N,N-Dimethyl-ethanol amine | — | 5.96 g | 2.98 g | — |
| 1,4-Diazabi-cyclo[2.2.2]-octane mono-borane (10% solids in Acetone) | — | — | 29.80 g | 59.60 g |

When the coating composition was mixed with either of the above curing agent solutions the following results were obtained which shows an increase in catalytic activity using the 1,4-diazabicyclo[2.2.2]octane-monoborane adduct, without adversely affecting the useable time in which the composition can be applied.

| Properties | Standard | Control | A | B |
|---|---|---|---|---|
| Stormer Viscosity at 75 KU (Krebs Units) | 2 hrs. | 5 hrs. | 4 hrs. | 5 hrs. |
| Tack-Free time at 45 micron dry film thickness | 5 hrs. | 9 hrs. | 7 hrs. | 5 hrs. |

EXAMPLE 3

Resin #1, the Anhydride Component was prepared as in Example 1. The anhydride equivalent weight was 518 gm. per equivalent, based on 100% solids.

| Resin #2 Preparation (Epoxy Component) | |
|---|---|
| Portion 1 | |
| Butylacetate | 244.67 g |
| Toluene | 25.51 g |
| Ethylacetate | 41.39 g |
| Portion 2 | |
| Glycidylmethacrylate | 233.12 g |
| Butylacetate | 62.29 g |
| Butylmethacrylate | 155.41 g |
| "Vazo" 67 initiator (from Du Pont) | 18.68 g |
| Portion 3 | |
| Butylacetate | 14.32 g |
| Propyleneglycolmonomethyletheracetate | 48.32 g |

Portion 1 was added to a reactor equipped with a stirred, thermometer, condenser, nitrogen purge and feed funnel, and heated to reflux. Portion 2 was premixed and added to the reactor over 2 hr. while maintaining reflux. Portion 3 was premixed and added over 30 min. after portion 2 was added. The batch was held at reflux for 30 additional min., then cooled and filled out. The epoxy equivalent weight was 236.7 g per equivalent, based on 100% solids.

| Resin #3 Preparation (Polyol Component) | |
|---|---|
| Portion 1 | |
| Methyl n-amyl ketone | 170.85 g |
| Portion 2 | |
| Methyl n-amyl ketone | 61.90 g |
| 75% t-Butylperacetate initiator | 27.74 g |
| Portion 3 | |
| Styrene | 143.88 g |
| Ethylmethacrylate | 143.88 g |
| Laurylmethacrylate | 115.12 g |
| Hydroxyethylacrylate | 172.63 g |

Portion 1 was added to a reactor equipped with a stirrer, thermometer, condenser, nitrogen purge and two feed funnels, and heated to reflux. Portion 2 was premixed and added to the reactor over 165 min. Portion 3 was premixed and added to the reactor over 150 min., starting at the same time as portion 2. The batch was held at reflux an additional 2 hr., then cooled and filled out. The hydroxy equivalent weight based on 100% solids was 386.6 g per equivalent.

Coating Compositions

The following coating compositions were made by thoroughly blending the following ingredients (all in grams):

| Ingredients | A | B |
|---|---|---|
| Resin #3 | 13.5 | 13.5 |
| 2-Methyl-1,4-diazabicyclo-[2.2.2]octane monoborane | 1.315 | 2.623 |
| "Tinuvin" 144 (a) | 6.3 | 6.3 |
| "Tinuvin" 328 (b) | 2.1 | 2.1 |
| Propyleneglycolmonomethyl ether | 4.1 | 4.1 |
| Reducer (c) | 12.72 | 12.23 |
| Resin #1 | 20.76 | 20.76 |
| Resin #2 | 9.78 | 9.78 |
| Denecol EX622 Epoxy Resin (d) | 3.15 | 3.15 |

(a) From Ciba-Geigy Corp., as a 10% solution in xylene.
(b) From Ciba-Geigy Corp., as a 30% solution in xylene.
(c) Reducer is:

| Butyl acetate | 19.8 |
|---|---|
| Propyleneglycolmonomethyl ether acetate | 13.2 |
| Xylene | 23.1 |
| n-Hexyl acetate | 43.9 |

(d) From Nagase Co.

Films of the above compositions were cast using a 0.010 inch draw down blade onto panels made of glass and thermoplastic polyolefin. The films had the following properties after curing at 25° C.:

| Modification | A | B |
|---|---|---|
| Gel Time (hr) | 37 | 26 |
| Persoz Hardness (after 7 days) | 147 | 152 |

The results clearly show the long gel times obtained when the monoborane of 2-methyl-1,4-diazabicyclo[2.2.2]octane is used as the curing agent.

EXAMPLE 4

Preparation of 1,4-Diazabicyclo[2.2.2]octane-Monoborane

Under dry nitrogen in a 3-neck, 5 L round bottom flask is charged with 336.6 grams (3 mol) 1,4-diazabicyclo[2.2.2]octane and 4 L dry acetonitrile. Sodium borohydride (113.5 grams, 3 mol) is added to the acetonitrile solution in a single portion. By means of a mechanical stirrer the suspension is stirred vigorously. Dry carbon dioxide gas is introduced over the surface of the solution. The temperature of the acetonitrile suspension is maintained at 40°–50° C. by means of a water cooling bath. The carbon dioxide addition is continued as long as there is uptake of the gas by the suspension. When the uptake of gas ceases the reaction is complete and 100 g of a dry filter aid (e.g. Celite ™) is added to the suspension as a single portion. The warm (40° C.) suspension is filtered under dry nitrogen pressure through a mat of filter aid. The filtrate is evaporated under reduced pressure to yield 360.2 g (95.3%) of the desired product as a free flowing powder. A sample of the borane adduct was recrystallized from hot toluene to yield a colorless crystalline solid, mp 162°–164° C. $^1$H NMR (CD$_2$Cl$_2$) δ 1.40 (q, 3H, BH$_3$), 2.86–2.95 (m, NCH$_2$); $^{13}$C NMR (CD$_3$CN) δ 6 46.84, 52.58 (CH$_2$). The mixed filter aid and sodium formate by-product is discarded.

EXAMPLE 5

Preparation of 2-methyl-1,4-Diazabicyclo[2.2.2]octane-Monoborane

Under dry nitrogen a 3-neck, 5L round bottom flask is charged with 378.7 grams (3 mol) 2-methyl-1,4-diazabicyclo[2.2.2]octane and 4L dry acetonitrile. Sodium borohydride (113.5 grams, 3 mol) is added to the acetonitrile solution in a single portion. By means of a mechanical stirrer the suspension is stirred vigorously. Dry carbon dioxide gas is introduced by bubbling under the surface of the solution. The temperature of the acetonitrile suspension is maintained at 40°–50° C. by means of a water cooling bath. The carbon dioxide addition is continued as long as there is uptake of the gas by the suspension. When the uptake of gas ceases the reaction is complete and 100 g of a dry filter aid (e.g. Celite ™) is added to the suspension as a single portion. The warm (40° C.) suspension is filtered under dry nitrogen pressure through a mat of filter aid. The filtrate is evaporated under reduced pressure to yield 375.0 g (90%) of the desired product as a free flowing powder. A sample of the borane adduct was recrystallized from ethyl acetate to yield a colorless crystalline solid, mp 78°–80° C. $^1$H NMR (CD$_2$Cl$_2$) δ1.15 (d, 3H, CH$_3$), 1.39 (q, 3H, BH$_3$), 2.33 (m, 1H, C$_3$CH), 2.75 (m), 2.99 (m); $^{13}$C NMR[$^1$H] (CH$_3$CN) δ, 18.6 (CH$_3$), 40.2, 48.7, 50.5 (C$_3$CH), 51.4, 52.7, 59.8. The filter aid and sodium formate by-product is discarded.

COMPARATIVE EXAMPLE 1

Preparation of 1,4-Diazabicyclo[2.2.2]octane-Monoborane

Under dry nitrogen a 4-neck, 500 mL round bottom flask is charged with sodium borohydride (18.9 g, 0.5 mol) and 250 mL ethyl acetate. 1,4-Diazabicyclo[2.2.-

2]octane (56.09 g, 0.5 mol) is added to the ethyl acetate solution in a single portion. By means of a mechanical stirrer the suspension is stirred vigorously. Dry carbon dioxide gas is introduced into the mixture by bubbling below the surface of the solution (simply passing the $CO_2$ gas over the vigorously stirred suspension also allows a rapid uptake of $CO_2$). The temperature of the ethyl acetate suspension is maintained at 20°–40° C. by means of a water cooling bath. The carbon dioxide addition is continued as long as there is uptake of the gas by the suspension. When the uptake of gas ceases the reaction is complete (4 hr.) and 250 mL deionized water is added to the suspension in a single portion. The water/ethyl acetate mixture is stirred for 5 minutes to insure complete mixing. By means of a separatory funnel, the water is separated from the ethyl acetate solution. The ethyl acetate solution is washed with 100 mL of 20% (by weight) $K_2CO_3$ and dried over anhydrous $K_2CO_3$. The ethyl acetate solution is then filtered through glass wool, to remove the $K_2CO_3$, and evaporated under reduced pressure to yield 19.24 g (31%) of the desired product as a free flowing powder of good purity, mp 162°–164° C. The $^1H$ NMR shows a spectrum consistent with the desired monoborane.

COMPARATIVE EXAMPLE 2

Preparation of
2-Methyl-1,4-diazabicyclo[2.2.2]octane-Monoborane

Under dry nitrogen a 4-neck, 500 mL round bottom flask is charged with sodium borohydride (18.9 g, 0.5 mol) and 250 mL ethyl acetate. 2-Methyl-1,4-diazabicyclo[2.2.2]octane (63.12 g, 0.5 mol) is added to the ethyl acetate solution in a single portion. By means of a mechanical stirrer the suspension is stirred vigorously. Dry carbon dioxide gas is introduced under the surface of the solution. The temperature of the ethyl acetate suspension is maintained at 20°–35° C. by means of a water cooling bath. The carbon dioxide addition is continued as long as there is uptake of the gas by the suspension. When the uptake of gas ceases (2 hr.) the reaction is complete and 100 mL of deionized water is added to the suspension as a single portion. The water/ethyl acetate mixture is stirred vigorously to insure complete mixing. The water is removed by means of a separatory funnel. The ethyl acetate solution is then washed with 100 mL of 20% (by weight) $K_2CO_3$ and dried over anhydrous $K_2CO_3$. The ethyl acetate solution is filtered through glass wool, to remove the $K_2CO_3$, and evaporated under reduced pressure to yield 55.7 g (79.5%) of impure (by $^1H$ NMR analysis) borane as a sticky white solid. The impure borane is recrystallized from toluene but some impurities remain so the impure product is further recrystallized from ethyl acetate to give 37.41 g (53%) of pure colorless crystalline product, melting point 77°–80° C.

Although preferred embodiments of the invention have been described hereinabove, it is to be understood that there is no intent to limit the invention to the precise embodiments described and that variations can be made without departing from the spirit and scope of the invention as claimed.

What is claimed is:

1. In a coating composition for finishing substrates wherein are mixed an anhydride polymer or copolymer having at least two anhydride groups, an epoxy polymer or copolymer having at least two epoxy groups and a curing agent, an improvement comprising the use of amine-borane adducts as the curing agent, and the coating composition is cured, without heating, at room temperature such that a primary reaction between the anhydride groups and epoxy groups occurs.

2. The improvement described in claim 1 wherein the anhydride polymer or copolymer and has a weight average molecular weight of 100,000 or less.

3. The improvement described in claim 1 wherein the epoxy polymer or copolymer, and has a weight average molecular weight of 100,000 or less.

4. The improvement described in claim 1 wherein the amine-borane adduct is a tertiary amine-borane complex.

5. The improvement described in claim 4 wherein the amine-borane adduct is selected from the group consisting of 1,4-diazabicyclo[2.2.2.]octane-monoborane, alkyl substituted 1,4-diazabicyclo[2.2.2]octane monoborane wherein the alkyl groups contain up to about 6 carbon atoms, N,N,N',N'-tetramethylethylenediamine-monoborane, N,N-dimethyl-1,3-propanediamine-monoborane, N,N-dimethyl ethanol amine-borane, N,N-diethyl ethanol amine-borane, N,N-dibutyl ethanol amine-borane, and N,N-diethyl hexanol amine-borane.

6. The improvement described by claim 5 wherein the amine borane adduct is selected from the group consisting of 1,4-diazabicyclo[2.2.2]octane-monoborane and alkyl substituted 1,4-diazabicyclo[2.2.2]octane-monoborane wherein the alkyl groups contain up to about 6 carbon atoms.

7. The improvement described in claim 6 wherein the amine-borane adduct is selected from the group consisting of 1,4-diazabicyclo[2.2.2]octane-monoborane and 2-methyl-1,4-diazabicyclo[2.2.2]octane monoborane.

8. The improvement described in claim 1 wherein the composition of the amine-borane adduct comprises from 1% to 6% by weight of the composition.

9. The improvement described in claim 7 wherein the composition of the amine-borane adduct comprises from 1% to 6% by weight of the composition.

10. The improvement described by claim 4 which has, blended in with the amine-borane adduct, a suitable quantity of borane-free amine.

11. The improvement described in claim 7 which has, blended in with the amine-borane adduct, a suitable quantity of borane-free amine.

12. A coating composition comprising 20% to 80% of an anhydride a polymer or copolymer with a weight average molecular weight of less than or equal to 100,000, having at least two anhydride groups, 80% to 20% of an epoxy polymer or copolymer with a weight average molecular weight of equal to or less than 100,000 containing at least two epoxy groups and 1% to 6% by weight of a tertiary organic amine-borane adduct as a catalyst, wherein the composition is cured, without heating, at room temperature and a primary reaction occurs between the anhydride groups of the anhydride polymer or copolymer and the epoxy groups of the epoxy polymer or copolymer.

13. The coating composition of claim 12 where the copolymer having at least two anhydride groups is selected from the group consisting of copolymers prepared from one or more of the monomers styrene, methacrylates, and acrylates with one or more of the monomers itaconic acid, itaconic anhydride, maleic anhydride, and isobutenyl succinic anhydride.

14. The coating composition of claim 12 wherein the copolymer having at least two epoxy groups is a copolymer prepared from monomers of methacrylate and glycidylmethacrylate in combination with polyglycidyl ethers of sorbitol.

15. The coating composition of claim 12 wherein the tertiary organic amine-borane adduct is selected from the group consisting of 1,4-diazabicyclo[2.2.2]octane-monoborane, alkyl substituted 1,4-diazabicyclo[2.2.2]octane-monoborane wherein the alkyl groups contain up to about 6 carbon atoms, N,N,N',N'-tetramethylethylenediamine-monoborane, N,N-dimethyl-1,3-propanediamine-monoborane, N,N-dimethyl ethanol amine-borane, N,N-diethyl ethanol amine-borane, N,N-dibutyl ethanol amine-borane, and N,N-diethyl hexanol amine-borane.

16. The coating composition of claim 12 wherein the tertiary organic amine-borane adduct is 1,4-diazabicyclo[2.2.2]octane-monoborane or 2-methyl-1,4-diazabicyclo[2.2.2]octane-monoborane.

* * * * *

UNITED STATES PATENT AND TRADEMARK OFFICE
CERTIFICATE OF CORRECTION

PATENT NO. : 5,034,464

DATED : July 23, 1991

INVENTOR(S) : Anthony J. Arduengo

It is certified that error appears in the above-identified patent and that said Letters Patent is hereby corrected as shown below:

at Col. 4, line 63, Change: (4.48 g, mp 164°165 C/)
to: (4.48 g, mp 164-165°C)

at Col. 10, line 30, Change δ 6 46.84
to: δ 46.84

Signed and Sealed this

Tenth Day of August, 1993

Attest:

MICHAEL K. KIRK

*Attesting Officer*   Acting Commissioner of Patents and Trademarks